United States Patent [19]

Starr et al.

[11] Patent Number: 5,258,295

[45] Date of Patent: Nov. 2, 1993

[54] FLUOROPHORE-ASSISTED CLONING ANALYSIS

[75] Inventors: Christopher M. Starr, Sonoma; John C. Klock, Mill Valley, both of Calif.

[73] Assignee: Glyko, Inc., Novato, Calif.

[21] Appl. No.: 840,739

[22] Filed: Feb. 25, 1992

[51] Int. Cl.⁵ .............................................. C12N 15/10
[52] U.S. Cl. .................................. 435/172.3; 435/7.4; 536/1.11
[58] Field of Search ...................... 435/172.3; 935/9, 1, 935/6, 15, 19, 79, 80

[56] References Cited

U.S. PATENT DOCUMENTS 5,035,786  7/1991  Brandley et al. ................ 204/182.1

FOREIGN PATENT DOCUMENTS

WO88/10422  12/1988  PCT Int'l Appl. .
WO91/12276  8/1991  PCT Int'l Appl. .
WO91/12520  8/1991  PCT Int'l Appl. .

OTHER PUBLICATIONS

Jackson, "The use of polyacrylamide-gel electrophoresis for the high resolution separation of reducing saccharides labelled with the fluorophore 8-aminonapthalene-1,3,6-trisulphonic acid," Biochem. J., 270:705–713 (1990).

Rothe, B., et al., Journal of General Microbiology, 135, 3087–3096 (1989).

Roggentin, P., et al., FEBS Letters, vol. 238, No. 1, 31–34 (1988).

Grange, J. et al., Journal of Applied Bacteriology, 47, 285–288 (1979).

BioTechniques, vol. II, No. 6, 739 (1991).

Hausler, A., et al., Glycobiology, vol. 2, No. 1, 77–84 (1992).

Miller, J. H., "Experiments in Molecular Genetics" 352–355 (1972).

Larsen, R. D., et al., Proc. Natl. Acad. Sci. USA, vol. 87, 6674–6678 (1990).

Luyten, G. P. M., et al., The Journal of Histochemistry and Cytochemistry, vol. 33, No. 9, 965–968 (1985).

Labrousse, H., et al., Journal of Immunological Methods, 48, 133–137 (1982).

Joziasse, D. H. et al., The Journal of Biological Chemistry, vol. 64, No. 24, 14290–14297, Aug. 25 (1989).

Kukowska-Latallo, J. F., et al., Genes & Development 4:1288–1303 (1990).

Larsen, R. D. et al., Proc. Natl. Acad. Sci. USA, vol. 86, 8227–8231 Nov. (1989).

*Primary Examiner*—Richard A. Schwartz
*Assistant Examiner*—James Ketter

[57] ABSTRACT

Various assays for the detection and quantitation of carbohydrate-interacting proteins are disclosed. Carbohydrate-interacting proteins include carbohydrate modifying enzymes and carbohydrate binding proteins. The assays employ a fluorophore-labelled carbohydrate substrate that either is capable of being structurally modified by the carbohydrate-modifying enzyme being assayed or changes its electrophoretic gel migration tube upon interaction with a carbohydrate-binding protein. Methods for cloning genes encoding carbohydrate-modifying enzymes are also disclosed.

13 Claims, No Drawings

FLUOROPHORE-ASSISTED CLONING ANALYSIS

FIELD OF THE INVENTION

The subject invention is in the field of carbohydrate chemistry. In particular, assays for carbohydrate-modifying enzymes, carbohydrate binding proteins and methods of cloning genes encoding these proteins.

BACKGROUND OF THE INVENTION

Carbohydrates play a number of important roles in the functioning of living organisms. In addition to their metabolic roles, carbohydrates may be covalently attached to numerous other entities such as proteins and lipids, i.e., glycoconjugates. For example, the carbohydrate portion of glycoproteins may critically affect the ability of glycoproteins to perform their biological functions, including such functions as ligand or receptor recognition.

The enormous potential for chemical and structural diversity among carbohydrates is provided, in part, by the way in which individual sugar units in a polysaccharide can be linked. A fundamental step in determining the three-dimensional structure of a polysaccharide or oligosaccharide is to determine the structure of these linkages. As a consequence of their diverse and important biological functions, aberrations in the synthesis, degradation, or modification of carbohydrates may give rise to altered biologic functions.

Many carbohydrate structures in nature are polysaccharides and oligosaccharides that are produced in a variety of related forms rather than existing in a single defined structure. These families of related carbohydrates are frequently found to be components of the same glycoconjugate. These families of glycoproteins that share the same polypeptide structure, but display variation in the glycosylation pattern have been referred to as glycoforms, Rademacher, et al., *Ann. Rev. Biochem.*, 57:789-838 (1988). Similarly, there is great diversity in the glycoforms associated with glycolipids, proteoglycans, and polysaccharides.

The concentration of individual carbohydrates in a sample may be measured by fluorophore-assisted carbohydrate electrophoresis. The technique of fluorophore-assisted carbohydrate electrophoresis is described in detail in U.S. Pat. No. 4,874,492, U.S. Pat. No. 5,104,508, filed Feb. 14, 1989, and Jackson, et al., *Anal. Bioch.* 270:705-713 (1990). Fluorophore-assisted carbohydrate electrophoresis permits the electrophoretic separation of a complex mixture of carbohydrates into distinct bands on a gel. Prior to electrophoresis, a carbohydrate mixture for analysis is treated with a charged fluorescent tag that combines with the reducing end of the carbohydrates for analysis. The fluorescent label permits the quantitative measurement of the labelled carbohydrates. The charged tag not only fluorescently labels the carbohydrates, but imparts an ionic charge, thus permitting hitherto uncharged carbohydrates to migrate in an electric field. After the carbohydrates have been labelled, the sample is subjected to polyacrylamide gel electrophoresis in order to separate and concentrate the labelled carbohydrates into bands. The separated carbohydrates may be visualized directly by fluorescence under U.V. light. Alternatively the separated carbohydrates may be visualized by means of laser-scanner photomultiplier tube system, a charge coupled device (CCD). CCD's are semiconductor imaging devices that permit the sensitive detection of emitted light. CCD's and their uses are described in U.S. Pat. Nos. 4,874,492 and 4,892,137. The image produced by the CCD may be subsequently transferred to a computer wherein the bands may be analyzed with the respect to parameters such as intensity, mobility, migration distance, and the like.

To date only a relatively small percentage of the carbohydrate-interacting protein, i.e., carbohydrate-modifying enzyme and carbohydrate-interacting protein, genes thought to exist in nature have been isolated. A principal reason for the limited number of successfully cloned carbohydrate-interacting protein genes is the lack of sensitive and specific assays for the identification of clones of interest during the screening of genetic libraries. Traditional methods for the cloning of these enzymes requires the use of monoclonal antibodies, polyclonal antibodies, or oligonucleotide hybridization probes based on protein sequence information for the screening of genetic libraries.

Thus, it is of interest to provide highly sensitive and highly specific assays for detecting and/or quantitating carbohydrate-interacting protein activity. Such highly specific and highly sensitive assays would have a number of uses that are difficult, or impossible, to achieve using currently available carbohydrate-interacting protein assay technology. These uses include the purification, detection and discovery of carbohydrate-interacting proteins having novel specificities. Highly specific and sensitive assays also find use in the cloning of genes encoding carbohydrate-interacting proteins.

SUMMARY OF THE INVENTION

One aspect of the present invention is to provide assays for detecting and/or quantitating carbohydrate-interacting proteins. The assays provided for employ a fluorescently labelled carbohydrate-substrate that is capable of being structurally modified by the activity of the carbohydrate-modifying enzyme being assayed or a fluorescently labelled carbohydrate substrate capable of specifically binding to a carbohydrate binding protein. By varying the structure of the substrate, a wide variety of carbohydrate-modifying enzymes and carbohydrate binding proteins may be assayed. The subject assays comprise the steps of contacting a sample for analysis with a fluorophore-labelled carbohydrate substrate and detecting changes in the structure of the substrate or changes in the electrophoretic gel migration rate of the substrate.

The structural modifications of the substrate caused by the actions of the carbohydrate-modifying enzyme being assayed may be detected by a variety of means. One aspect of the invention is to measure alterations in the structure of the substrate by fluorophore-assisted carbohydrate electrophoresis. Another aspect of the invention is to detect changes in substrate structure by measuring increases in the amount of a fluorescent carbohydrate-substrate moiety found in solution, when the substrate is initially present in insoluble form by conjugation to a carrier or subsequently removed from the soluble phase by an antibody, and increases in the amount of the soluble fluorophore-labelled moiety are measured by fluorimetry, fluorophore assisted carbohydrate electrophoresis or other similar techniques. The carbohydrate-substrate may be rendered insoluble by conjugation to a carrier particle or by binding to antibodies. Fluorophores suitable for labeling carbohydrates so as to produce assay substrates include 8- aminonapthalene-1,3,6-trisulphonic acid, 1-amino-6,8-disulphonic acid, 1-amino-4-naphthalene sulfonic acid, lucifer yellow, and 2-aminoacridone.

Another aspect of the subject invention is to provide assays for the detection and/or quantification of carbohydrate binding proteins, in which the presence of the carbohydrate binding protein being assayed is detected by changes in the carbohydrate substrate gel migration rate caused by interaction of the substrate with the carbohydrate binding protein being assayed, the migration rate changes being detected by fluorophore assisted carbohydrate electrophoresis.

Another aspect of the subject invention is that assays may be provided for enzymes that have not yet been discovered, by producing carbohydrates that may be used as substrates for carbohydrate-interacting proteins with the desired specificity.

Still another aspect of the subject invention is to provide methods of cloning genes or cDNAs encoding carbohydrate-interacting proteins. The cloning methods provided employ the carbohydrate-interacting protein assays of the subject invention. The assays may be performed on extracts of cells containing portions of the gene library of organisms containing genes encoding carbohydrate-modifying enzymes of interest.

Another aspect of the subject invention is to provide for automated assays for carbohydrate-interacting protein activity.

Still another aspect of the subject invention is to provide kits for performing assays for carbohydrate-interacting proteins and kits for cloning genes and cDNAs encoding carbohydrate-interacting proteins.

Another aspect of the subject invention is to provide for genes and cDNAs encoding carbohydrate-interacting proteins, host cells for the recombinant DNA production of carbohydrate-interacting proteins, and carbohydrate-interacting proteins produced by the host cells.

DESCRIPTION OF THE SPECIFIC EMBODIMENTS

The use of fluorophore-assisted carbohydrate electrophoresis or similar techniques for separating fluorophore-labelled carbohydrates in order to screen genetic libraries for genes and cDNAs encoding carbohydrate-interacting proteins is referred to herein as fluorophore-assisted cloning analysis, or "FACA." FACA is in part based on a cloning strategy that allows for the identification of prokaryotic or eukaryotic genetic library host cells that express carbohydrate-interacting protein(s) encoded by cloned genes by assaying for the activity of the carbohydrate-interacting protein of interest. Because FACA allows for the selection of nucleotide sequences encoding functional proteins, FACA may eliminate the tedious task of constructing full-length clones from partial sequences which is often required using traditional cloning methods. The subject invention also provides assays for the detection and quantitation of carbohydrate-interacting protein activity. The term "carbohydrate-interacting protein" includes both carbohydrate-modifying enzymes and carbohydrate binding proteins. The term "carbohydrate-modifying enzyme" refers to those enzymes having a carbohydrate substrate. Carbohydrate-modifying enzymes may alter the structure of the substrate carbohydrates in a variety of ways including the hydrolysis of linkages between saccharide units, the formation of linkages between saccharide units, and the addition of various side groups to carbohydrate molecules. Carbohydrate-modifying enzymes include hydrolases, lyases, acetylases, sulfatases, phosphatases, kinases, epimerases, methylases, amidases, transaminases, transferases, and the like. The term "carbohydrate binding protein" refers to proteins capable of binding carbohydrates with relatively high specificity and affinity. Carbohydrate binding proteins include lectins, carbohydrate transport proteins, receptors and the like. The term "activity" when used in conjunction with carbohydrate-interacting proteins may refer to the enzymatic activity of carbohydrate-modifying enzymes and the binding activity of carbohydrate binding proteins. The term "substrate" as used herein, unless indicated otherwise, refers both to substrates for enzymes and ligands for binding to carbohydrate binding proteins.

Assays of the subject invention involve the step of contacting a solution suspected of containing a carbohydrate-interacting protein of interest with a carbohydrate-substrate selected to detect interactions with the protein of interest on the basis of either changes in structure of the substrate or changes in the gel migration rate of the substrate as detected by fluorophore assisted carbohydrate electrophoresis. The structure of the carbohydrate-substrate will vary in accordance with the identity of the carbohydrate-interacting protein of interest. The carbohydrate portion of a carbohydrate-substrate, i.e., the portion of the molecule other than the fluorophore label, may consist entirely of carbohydrate or be a glycoconjugate, e.g., a glycoprotein, glycolipid, glycosaminoglycan, or the like. Carbohydrate-substrates are selected so as to be capable of being structurally altered by the carbohydrate-modifying enzyme of interest, or in the case of assays for carbohydrate-binding proteins, the carbohydrate substrate is selected so that the substrate specifically binds to the carbohydrate binding protein of interest. Assay substrates are carbohydrates labelled with a fluorophore that is either charged or coupled with a charge imparting species when the fluorophore itself is uncharged. Suitable fluorescent labels for producing substrates of the subject invention are those fluorophore labels that find use in fluorophore assisted carbohydrate electrophoresis and include: 8-aminonapthalene- 1,3,6-trisulphonic acid (ANTS), 1-amino-4-naphthalene sulfonic acid (ANSA), 1-amino-6,8-disulphonic acid (ANDA), lucifer yellow, and 2-aminoacridone. A description of fluorophores suitable for use in generating substrates of the subject invention and methods for coupling the fluorophore to carbohydrates can be found in U.S. Pat. No. 5,035,786, filed Feb. 16, 1990, U.S. patent application Ser. No. 07/721,120, filed Jun. 26, 1991, PCT Patent Application filed Dec. 19, 1991, and UK patent application Serial No. GB/90/01448, filed Sep. 20, 1990 and published as PCT application WO91/05256.

When used in assays for carbohydrate-modifying enzymes, a portion of the substrate necessarily contains a region capable of being structurally altered by the carbohydrate-modifying enzyme being assayed. The term "structurally altered" includes any change in the structure of the carbohydrate-substrate, including the addition of atoms, the removal of atoms, and structural rearrangements.

Assay substrates may be prepared for detecting and quantifying the activity of carbohydrate-modifying enzymes that have not yet been discovered by producing substrates that have a structure of which at least a portion is similar or identical to the naturally occurring substrate for the enzyme of interest. For example, an enzyme that specifically hydrolyses a β1–4 linkage between D-fucose and D-glucose may be detected by using a substrate that is a polysaccharide having at least one β1–4 linkage between D-fucose and D-glucose (and is labelled with a suitable fluorophore).

In addition to finding use in assays for the detection and measurement of carbohydrate-modifying enzyme activity, fluorophore-labelled carbohydrate substrates may be used to detect and quantitate various carbohydrate-binding proteins, such as lectins. Carbohydrate substrates for use in assays for carbohydrate binding proteins are selected so as to have a structure (excluding the fluorophore portion) similar or identical to naturally occurring ligands for the carbohydrate binding protein of interest. Assays for carbohydrate binding proteins include the steps of contacting a sample for analysis with a fluorophore-labelled carbohydrate substrate and subsequently measuring changes in the gel mobility rate of the carbohydrate attributable to the presence of carbohydrate binding proteins of interest in the sample for analysis, the mobility rate changes being measured by fluorophore-assisted carbohydrate electrophoresis. The interaction between a carbohydrate-binding protein and a carbohydrate that specifically binds to the given carbohydrate-binding protein may result in a change, typically a decrease, in the migration, i.e., mobility rate of the carbohydrate, as measured by fluorophore-assisted carbohydrate electrophoresis. The amount of carbohydrate binding protein present in a sample for analysis may be measured quantitatively by measuring the intensity of any newly formed band caused by alterations in the gel migration rate of the labelled carbohydrate substrate. Assays for carbohydrate binding protein activity may be used to discover new carbohydrate binding proteins by using substrates that have a structure of which at least a portion is similar or identical to the naturally occurring ligand for the carbohydrate-binding protein of interest.

Alterations in carbohydrate substrate structure attributable to the activity of carbohydrate-modifying enzymes may be detected by a variety of means. A particularly preferred method of detecting alterations in the structure of a fluorophore labelled carbohydrate-substrate caused by the carbohydrate-modifying enzymes being assayed is by means of fluorophore-assisted carbohydrate electrophoresis. Fluorophore-assisted carbohydrate electrophoresis may also be used in assays to measure carbohydrate-binding proteins because the ability of the technique to detect changes in gel migration rates caused by interactions between carbohydrate binding proteins and their target carbohydrates.

The technique of fluorophore assisted carbohydrate electrophoresis is described in detail in U.S. Pat. No. 4,874,492 and in co-pending U.S. Pat. No. 5,104,508, filed Feb. 14, 1989, Jackson, P., *Anal. Biochem.* 196:238–244 (1991) and Jackson, P., *Biochem. J.* 270:705–713 (1990). Fluorophore assisted carbohydrate electrophoresis provides for the electrophoretic separation of a complex mixture of fluorophore-labelled carbohydrates into distinct bands on a gel. The carbohydrates separated by fluorophore-assisted carbohydrate electrophoresis may vary with respect to each other in terms of size, structure, and charge. Fluorophore-assisted carbohydrates electrophoresis also permits the separation of carbohydrates that have identical molecular weights but structurally differ with respect to one another, for example as stereoisomers or as an enantiomers. The results of fluorophore assisted carbohydrate electrophoresis in assays for carbohydrate-interacting proteins may be visualized by any of the methods used to visualize the results of fluorophore assisted carbohydrate electrophoresis, the use of CCds being particularly preferred.

Carbohydrate substrates used in assays for carbohydrate-interacting proteins to be used in conjunction with fluorophore-assisted carbohydrate electrophoresis may be labelled with a suitable fluorophore either before or after the step of mixing the sample for analysis with the substrate. In a preferred embodiment of the invention, carbohydrate substrates are labelled with a fluorophore before the step of mixing the substrate with same for analysis, i.e., pre-labelling. Among the advantages of pre-labelling substrates is the avoidance of the spurious labelling of non-substrate molecules in the sample for analysis.

Structural modifications of carbohydrate substrates by carbohydrate-modifying enzymes may be detected without fluorophore-assisted carbohydrate electrophoresis. Alternative methods of detecting structural changes in carbohydrate substrates include various forms of chromatography, chromatofocusing, capillary electrophoresis, and the like. Additional methods of measuring changes in the structure of carbohydrate substrates that are mediated by carbohydrate-modifying enzymes being assayed are possible when the carbohydrate substrate is present in an insoluble form or in a form that may be readily converted to an insoluble phase. Insoluble substrates may be prepared by conjugating labelled carbohydrate substrates to insoluble carriers such as macroscopic beads, composed of components such as polyacrylamide, agarose, polystyrene, and the like, so that upon interaction of the insoluble substrate with the carbohydrate-modifying enzyme of interest, a soluble fluorophore labelled carbohydrate moiety is liberated from the insoluble substrate. The term "moiety" refers to a molecule that consists of a portion of a carbohydrate substrate; a particular "moiety" is defined with respect to the labelled carbohydrate substrate from which it is derived. The soluble fluorophore-labelled moiety may then be measured without employing additional separation steps, e.g., by fluorometry, spectrophotometry, or by separation methods such as fluorophore assisted carbohydrate electrophoresis, or other similar techniques. Similarly, soluble carbohydrate substrates may be rendered insoluble by the addition of an antibody (or similar multi-valent specific-binding molecules) specific for a portion of the carbohydrate substrate that is not modified by the enzyme of interest. Thus an antibody (or similar molecule) may be used to remove the substrate from the soluble phase, thereby permitting the detection of the "liberated" soluble fluorophore-labelled carbohydrate moieties by fluorometry, fluorophore assisted carbohydrate electrophoresis, or the like.

Assays for carbohydrate-interacting proteins using fluorophore-labelled carbohydrate substrates may be either quantitative or qualitative. Fluorophore-assisted carbohydrate electrophoresis permits the quantitative measurement of fluorescently labelled carbohydrates on the basis of band fluorescence intensity. Both quantitative and qualitative assays may be performed using similarly prepared samples for analysis containing substantially equal quantities of sample, fluorophore-labelled carbohydrate substrate, and other reaction reagents. Assays are preferably performed in parallel for equal periods of time. Performing assays for specific periods of time may require terminating the assay. The activity of a carbohydrate-modifying enzyme being assayed may be terminated in a variety of ways, including shifting the pH of the assay solution, adding chelating agents, incubation at high temperature, adding competitive inhibitors, adding denaturing agents, and separating the reaction mixture by electrophoresis. Assays are preferably performed with both negative and positive controls. Controls include performing assays without the addition of sample suspected of containing the enzyme of interest and assays known to contain the enzyme of interest. Similarly, positive and negative assay controls are preferably performed in conjunction with assays for carbohydrate binding proteins. Quantitative assays may be performed to measure the rate at which a fluorophore-labelled substrate is structurally altered by the carbohydrate-modifying enzyme of interest; rate measurements may require a measurement of changes in the amount of fluorescence of either the fluorophore-labelled carbohydrate substrate or the fluorophore-labelled carbohydrate substrate modification product as a function of time. Assays may also be performed in conjunction with standards of known quantity in order to determine the actual amount of substrate that is structurally altered by the carbohydrate-modifying enzyme of interest during a given assay. Standards may consist of the substrate before and/or after structural alteration by the carbohydrate-modifying enzyme being assayed. In assays for carbohydrate binding proteins, assays may also contain quantitative standards, i.e., known quantities of carbohydrate binding protein of interest.

The assays of the subject invention may employ various co-factors in the assay solution. Co-factors may include ions necessary for the activity of the enzyme. Co-factors may also include various inorganic groups and organic groups, including carbohydrates, that associate with the carbohydrate-modifying enzyme of interest so as to modify the fluorophore-labelled carbohydrate substrate, i.e., donors, nucleotide sugar complexes such as ADP-glucose, ATP, and the like.

The assays of the subject invention may also employ various buffers in order to optimize the activity of the carbohydrate-modifying enzyme of interest. In the case of newly discovered carbohydrate-interacting proteins, the buffer, and the pH buffering range may be systematically varied so as to optimize activity.

An advantage of the assays of the subject invention is the ability to simultaneously perform assays for several different carbohydrate-interacting proteins within the same reaction mixture. In order to perform multiple assays simultaneously within the same reaction mixture, a plurality of fluorophore-labelled carbohydrate substrate are added to the sample for analysis and the reaction mixture is subsequently analyzed by fluorophore assisted carbohydrate electrophoresis. When a plurality of fluorophore-labelled carbohydrate substrates are added to a single reaction mixture, the substrates differ in structure from one another and may be labelled with either the same or different fluorophores. Typically, one fluorophore-labelled carbohydrate substrate is added to the reaction mixture for each carbohydrate-interacting protein being assayed; however, fluorophore-labelled carbohydrate substrates may be used that serve as substrates for more than one carbohydrate-interacting protein of interest. When a plurality of carbohydrate-interacting proteins are being assayed simultaneously, the various fluorophore-labelled carbohydrate substrates may be added individually or in solution(s) containing more than one fluorophore-labelled carbohydrate substrate. Analysis of the results of assays in which multiple fluorophore-labelled carbohydrate substrates are employed is preferably performed in conjunction with the use of computer programs for analyzing banding pattern changes caused by the presence of one or more carbohydrate-interacting proteins of interest in samples for analysis.

The subject invention provides for several methods of cloning genes encoding carbohydrate-interacting proteins. Cloning methods of the subject invention employ the above-described carbohydrate-interacting protein assays to identify library host cells containing genes encoding carbohydrate-interacting proteins of interest.

Methods of preparing genetic libraries are well known to those skilled in the art of molecular biology. Among the many widely available publications describing how to prepare genetic libraries are *Molecular Cloning: A Laboratory Manual*, 2nd Ed., Sambrook et al, Cold Spring Harbor Laboratory Press, Cold Spring Harbor, N.Y. (1989), and *Guide to Molecular cloning Techniques: Methods in Enzymology, Volume* 192, Berger and Kimmel, Academic Press, San Diego, Cal. (1987). The term "genetic library" as used herein refers to the aggregate sum of various nucleotide sequences from a "source organism" present in a vector and contained within host cells. The term "library isolate" refers to a collection of host cells containing essentially the same nucleotide sequence derived from the library source organism.

Most types of gene libraries may be screened using the described carbohydrate-interacting protein assays, provided that the library host cells are capable of expressing the carbohydrate-modifying gene of interest (or portions thereof). Library host cells may be either prokaryotic or eukaryotic. Suitable library host cells include *E. coli, S. cerevisiae*, as well as various mammalian cells. Genetic libraries suitable for screening may be produced using most available library vectors including plasmids, cosmids, retroviral vectors, phage vectors, yeast artificial chromosome vectors (YACs), λ phage vectors, SV40 based vectors, and the like. Particularly preferred vectors for use in genetic libraries to be screened for carbohydrate-interacting protein encoding genes are vectors designed to functionally express source organism nucleic acid sequences inserted into the vector. Suitable libraries for screening may be either genomic or cDNA. Subtracted cDNA libraries may also be used for screening. Genomic libraries preferably represent at least 90% of the genome of the same organism. Genetic libraries may be prepared from the nucleic acids of a variety of source organisms, either prokaryotic or eukaryotic, including bacterial cells, plant cells, fungal cells, and mammalian cells.

In addition to being useful for screening host cells from various genetic libraries, the assays of the subject invention may be used to detect carbohydrate-interacting protein activity of interest in Xenopus oocytes injected with nucleic acids, typically mRNA fractions, suspected of encoding carbohydrate-interacting proteins of interest. The use of other transient expression systems to produce carbohydrate-interacting proteins for detection is also contemplated for use in detecting nucleic acid sequences of interest.

In fluorophore assisted cloning analysis (FACA), extracts of library isolate cells suspected of containing source organism genes (or portions thereof) encoding carbohydrate-interacting proteins of interest are assayed for the activity of these proteins by using the previously described carbohydrate-interacting protein assays so as to detect the expression or lack of expression of the carbohydrate-modifying gene of interest in the host cell. Methods for producing suitable extracts will vary in accordance with the type of host cell employed. Generally, the host cells will need to be lysed and/or solubilized in order to release the carbohydrate-interacting proteins of interest for use in the assay. Methods for producing extracts from host cells are well known in the art; these methods of producing extracts are substantially the same as the well known methods of producing extracts used for protein purification. Suitable methods of producing extracts for use with the assays of the subject invention are described, for example, in *Guide to Protein Purification* Methods in Enzymology Vol. 182, edited by Deutscher, Academic Press Inc., San Diego, Cal. (1990).

It may be particularly advantageous to prepare extracts from one or more distinct host cell isolates so as to provide for a "pooled" extract from several library isolates. Because of the high sensitivity and specificity of the assays of the subject invention, very low levels of activity of carbohydrate-interacting proteins of interest may be detected in such pooled extracts. By using pooled extracts, the number of carbohydrate-interacting protein assays that are required for identifying clones containing carbohydrate-modifying enzyme genes of interest is reduced. For example, a cosmid library containing 10,000 clones (representative of 99% of the genome of the source organism) may be divided into pools of 500 colonies each. Extracts are subsequently produced from each of these pools of 500 clones and assayed performed on each one of the twenty pools. Since the carbohydrate-modifying enzyme gene of interest would be present in only a few library isolates, typically only one, or at most two pools would be expected to display the activity of the carbohydrate-modifying enzyme of interest. The library isolates from which the pooled extract is formed could then be further subdivided, and additional assays performed on the subpools. Thus the number of assays required for identifying genetic library isolates containing carbohydrate-modifying genes of interest is minimized.

The screening of genetic libraries for genes encoding carbohydrate-modifying enzymes of interest may also be performed using a preliminary screen with an indicator followed by a secondary screening using the previously described assays for carbohydrate-modifying enzymes. By "indicator" it is intended a chromogenic or fluorogenic substrate that may incorporated into growth medium used for the growth of a genetic library (or subsequently applied to the genetic library, e.g., by spraying). The indicator produces a color change in response to various enzyme activities or localized pH changes in the host cell growth medium. Various chromogenic indicators exist for detecting the activity of carbohydrate-modifying enzymes, for example, X-gal for detecting β-galactosidase, or tetrazolium for detecting fermentation of a given sugar; however, chromogenic indicators are not specific for particular carbohydrate-modifying enzymes. Thus chromogenic (or fluorogenic) indicators may be used in a preliminary screen of a genetic library in order detect library isolates suspected of containing carbohydrate-modifying genes of interest. The number of fluorophore-labelled carbohydrate substrate assays required for identifying those library isolates containing the carbohydrate-modifying genes of interest is minimized by employing a preliminary screen with indicators.

The assays of the subject invention may be employed in various purification schemes for carbohydrate-interacting proteins of interest. The high specificity of the assays of the subject invention permits the identification of a carbohydrate-interacting protein of interest throughout the purification scheme thus avoiding the possibility of purifying carbohydrate-interacting proteins with overlapping activities for a less specific substrate.

Proteins encoded by genes isolated, at least in part, by fluorophore-assisted carbohydrate cloning analysis may be expressed using well-known methods of recombinant DNA technology. Among the many publications teaching methods for the expression of genes after they have been isolated is "Gene Expression Technology", *Methods in Enzymelogy, Volume:* 185, edited by Goeddel, Academic Press, San Diego, Cal., (1990). Proteins encoded by genes isolated, at least in part, by fluorophore-assisted carbohydrate cloning analysis may be expressed in a variety of host cells either prokaryotic or enkaryotic. Host cells may be from species the same or different than cells from which the recombinantly expressed genes are naturally present, i.e., endogenous. Advantages of producing carbohydrate modifying proteins by recombinant DNA technology include obtaining highly enriched sources of the proteins for purification and the availability of simplified purification procedures.

Carbohydrate-interacting proteins produced by recombinant DNA technology have a variety of uses depending on the activity of the particular protein. Carbohydrate modifying enzymes may be used to analyze the structure of unknown carbohydrates by virtue of their interactions with specific structures within the carbohydrate. Carbohydrate-interacting proteins may be therapeutically administered to patients suffering from carbohydrate metabolism diseases attributable to decreased levels of a functional carbohydrate-interacting protein. Carbohydrate-interacting proteins may also be used in various industrial processes such as the manufacture of food, beverages and chemicals.

In addition to finding use in the recombinant DNA production of carbohydrate-interacting proteins, genes encoding carbohydrate-interacting proteins may be used as sources of hybridization probes for detecting the presence of normal or mutant copies of carbohydrate-interacting protein genes of interest. Nucleotide sequences of carbohydrate-interacting proteins may also be useful in various forms of therapy for genetically based diseases, including replacement gene therapy and antisense RNA production.

The assays of the subject invention may be used to discover new carbohydrate-interacting proteins having a desired activity by employing fluorophore labelled carbohydrate-interacting with a structure capable of specifically interacting with the sought after protein. Extracts from various cells, including plant, animal, fungal, and bacterial cells may be used in attempts to discover carbohydrate proteins with a desired activity and the genes encoding these proteins.

Various steps in the subject assays for carbohydrate-modifying enzymes and fluorophore assisted cloning analysis may be modified by automation. Automation has numerous advantages including improved reproducibility, improved accuracy, reduction in the amount of skilled manpower needed to achieve the same results, and the ability to perform procedures 24 hours a day. In general, many of the liquid handling steps in assays for carbohydrate-modifying enzymes and fluorophore assisted cloning analysis may be automated. Steps suitable for automation include the preparation of samples for analysis, the measuring of liquid volumes, the transfer of liquids, the mixing of solutions, the correlation of assay reaction containers with assay results, agitation of solutions, electrically switching, and the interpretation of assay results.

The subject invention also provides for kits for performing carbohydrate-interacting protein activity assays, and for the cloning of genes encoding carbohydrate-interacting proteins. Kits may include fluorophores, fluorophore-labelled carbohydrate substrates, electrophoresis reagents, antibodies, CCDs, computer software for analysis of results, premeasured reagents, standards for analysis (including enzyme standards and modified substrates standards, i.e., substrates both before and after structural alterations by the carbohydrate-modifying enzyme of interest), gel fluorescence illumination equipment, chromogenic indicators, photographic equipment, reagent containers, vectors for generation of genetic libraries, library host cells, and media for the growth of the genetic library. Kits also preferably contain instructions. Instructions are directed to various steps in performing the assays and/or genetic library screening. Kit instructions preferably describe the steps of contacting the sample for analysis with a fluorophore-labelled carbohydrate substrate and/or measuring the gel mobility rate changes of carbohydrate substrates caused by substrate binding to carbohydrate binding proteins and/or measuring changes in the structure of fluorophore-labelled carbohydrate substrates caused by carbohydrate-modifying enzymes. Among other things, kit instructions may also describe at least one or more of the following steps, fluorophore labelling of carbohydrates for use as substrates, collection of samples for analyzing, separating carbohydrates by fluorophore-assisted carbohydrate electrophoresis, using software for the analysis of fluorophore-assisted carbohydrate analysis, and preparation of samples for use in assays for carbohydrate modifying enzymes.

The following example is offered for the purposes of illustrating, not limiting, the invention.

EXAMPLE

This experiment was performed in order to demonstrate that bacterial cells expressing $E.\ coli$ $\beta$-galactosidase encoded in an independently replicating plasmid can be distinguished from bacterial cells that do not express $\beta$-galactosidase using assays with fluorophore-labelled carbohydrate substrates.

Reagents

5nMoles of ANTS (8-aminonapthalene-1,3, 6-trisulphonic acid) labelled lactose (Galactose-$\beta$1-4Glucose)
$E.\ coli$ DH5 cells lacZDM15 (Life Technologies, Gaithersburg Md.)
pGEM-3Zf-plasmid (Promega, Madison Wis.)
X-gal, 5-bromo-4-chloro-3-indolyl-B-D-galactoside (Stratagene, La Jolla, Cal.)

Methods

Performing FACA

Approximately 5 nanomoles of purified lactose was placed in a microcentrifuge tube and dried using a centrifugal vacuum evaporator (c.v.e.). To the dried sample was added 5 $\mu$l of 0.2M ANTS solution in acetic acid/water (3:17 v/v) and 5 $\mu$l of 1.0M NaCNBH$_3$ solution in dimethyl sulphoxide (DMSO). The solution was vortex mixed, centrifuged at 10,000 g (to ensure all the reactants are in the tips of the tubes), and incubated at 37° C. for 4 hours. The reaction mixture was dried under vacuum in a c.v.e. at approximately 45° C. and dissolved in water, so that the concentration of lactose was 100pmol/$\mu$l.

The DH5 strain of $E.\ coli$ cells were streaked out on LB plates and grown overnight at 37° C. DH5 express the lacZDM15 phenotype and do not express $\beta$-galactosidase. Individual colonies were used to seed 50 mls of LB broth and cells were grown in suspension overnight. Cells were centrifuged at 5,000 rpm and made competent for transfection with CaCl$_2$ using published procedures (Hanahan, D. 1983 $J.\ Mol.\ Biol.$ 166:557 (1983)). Competent cells were transfected with the transcription plasmid pGEM3ZF-. pGEM3ZF- contains the LacZ gene that encodes $\beta$-galactosidase and therefore cells transformed with the pGEM3ZF- plasmid express $\beta$-galactosidase. To confirm the expression of $\beta$- galactosidase by cells transfected with pGEM3ZF-, both non-transfected cells and transfected cells were grown in LB plates containing X-gal. In this culture system, colonies expressing $\beta$-galactosidase hydrolyze X-gal to yield a blue precipitate giving these colonies a blue color while colonies not expressing the glycosylase activity remain white. As expected, DH5 cells that had been transfected with pGEM3ZF- showed the blue phenotype when streaked on plates of LB plus X-gal, confirming the presence of $\beta$-galactosidase activity while the non-transfected cells remained white.

In order to determine whether the presence of the plasmid derived $\beta$-galactosidase activity in transfected cells could be detected and measured using fluorophore-labelled carbohydrate substrates, extracts were prepared from colonies transfected with pGEM3ZF- and from non-transfected cells. $\beta$-galactosidase was released from cellular compartments by sonication using a Bronson 450 sonicator in sonication buffer (10 mM Tris-HCl pH 7.6, 10 mM MgOAc, 200 mM NaCl, and 0.1 mM EDTA). Extracts were then diluted in 0.2M NaPO4, 0.1M citrate pH 7.8 containing a final concentration of 5 nmoles ANTS labelled lactose and incubated for 15 minutes at 37° C. Proteins in the extract were precipitated using 3 volumes of ice-cold ethanol and following centrifugation the ethanol supernatant containing the sugars was evaporated to dryness using a c.v.e. The dried pellets were resuspended in 50 $\mu$l gel loading buffer and fluorophore-assisted carbohydrate electrophoresis was performed as described below. The labelled samples are subjected to PAGE using a minigel electrophoresis apparatus. The electrophoretic buffer used is based on the Tris/HCL/glycine discontinuous system of Laemmli, with 10% SDS omitted throughout. The polyacrylamide gel consists of 35% (w/v) acrylamide containing 1% (w/v) NN'methylenebisacrylamide, respectively, as a cross linker. The polymerization of the gel was initiated by the addition of 20 $\mu$l 10% (w/v) ammonium persulphate solution and 10 $\mu$l of N,N,N,'N'-tetramethylene-diamine/ 12 ml of gel solution. The resolving gel size is 80 mm high ×80mm wide×approx. 0.5 mm thick. A stacking gel was used. The sample wells were 7 mm wide. Samples were electrophoresed at 30 mA for 120 minutes until the buffer front reached approximately 5-10 mm from the gel base. All amperages were held constant. The gels were cooled to 5°-7° C. by the surrounding stirred lower electrode buffer.

The gel was photographed using a cooled CCD camera system, specifically the Astromed CCD camera, described in U.S. Pat. No. 4,874,492. The gel was also photographed either through the glass cassette and after removal from its cassette (placed in a cassette holder within the imager). The gel cassette was placed on a U.V. light box (a Transilluminator, type TM 40) with a maximum emission wavelength of 302 nm and a power of approximately 700 $\mu W/cm^2$. A Polaroid type 55 film (ISO 50), a Wratten 8 gelatin filter (Kodak), an aperture of f4.5 and an exposure time of 50 seconds were used to image the gel.

Results

The carbohydrate banding patterns observed demonstrated that ANTS-labelled lactose from *E. coli* colony extracts could serve as a substrate of β-galactosidase and cells expressing β-galactosidase (the blue colonies) could readily be distinguished from cells not expressing β-galactosidase (the "white" colonies) based on the appearance of fluorophore-labelled glucose, the labelled product, i.e., labelled-moiety, resulting from β-galactosidase hydrolysis of lactose. The analyzed gel contained five lanes, I-V. Lane I demonstrated the migration of glucose polymers ranging from Glucose to 8 Glucose residues; this lane was used to measure migration distances. Lane V showed the migration of fluorophore-labelled lactose, the substrate of β-galactosidase used in these experiments. Lane II showed the sugars released by incubating the white colony supernatant, i.e., extract, with 125 milliunits of purified *E. coli* β-galactosidase obtained from commercial sources. The appearance of a band corresponding to glucose in lane II was attributable to the hydrolysis of the labelled lactose substrate by the purified β-galactosidase. The absence of this glucose band in an assay with the white colony supernatant alone demonstrated that the enzyme is not present in these cells (lane III). Lane IV contained the sugars released by the blue colony supernatant; Lane IV showed the release of labelled glucose and demonstrated that the β-galactosidase activity present in these cells is easily detected with fluorophore-labelled carbohydrate substrates. These results indicate that assays for carbohydrate-modifying enzymes using fluorophore-labelled carbohydrate substrates can be used to distinguish bacterial colonies expressing a specific glycosidase activity from other colonies that do not and therefore forms the basis of a highly sensitive (detection of 0.1 milliunit enzyme) and specific screening assay for identifying colonies expressing specific enzyme activities. By using a mixture of labelled substrates, a population of several glycosidases present in the same sample can be simultaneously analyzed.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The foregoing written specification is considered to be sufficient to enable one skilled in the art to practice the invention. Indeed, various modifications of the above-described modes for carrying out the invention which are obvious to those skilled in the fields of biochemistry or chemistry or related fields are intended to be within the scope of the following claims.

What is claimed is:

1. A method for isolating a gene encoding a carbohydrate-interacting protein from a genetic library, said method comprising the steps of,
   preparing an extract of host cells comprising at least a portion of said genetic library,
   contacting said extract with a fluorophore-labelled carbohydrate substrate, and
   detecting an interaction between said protein and said substrate.

2. A method according to claim 1, wherein said host cells are prokaryotic.

3. A method according to claim 1, wherein said host cells are eukaryotic.

4. A method according to claim 1, said method further comprising the steps of, exposing said genetic library to an indicator prior to said step of preparing an extract.

5. A method according to claim 4, wherein said carbohydrate interacting protein is a carbohydrate-modifying enzyme and said detecting step is measuring changes in the structure of at least a portion of said substrate.

6. A method according to claim 5, wherein said structure change measuring step comprises performing fluorophore assisted carbohydrate electrophoresis.

7. A method according to claim 1, wherein said carbohydrate-interacting protein is a carbohydrate-modifying enzyme and said detecting step is measuring changes in the structure of at least a portion of said substrate.

8. A method according to claim 1, wherein said carbohydrate-interacting protein is a carbohydrate binding protein and said detecting step is measuring changes in the electrophoretic mobility of at least a portion of said substrate.

9. A method according to claim 8, wherein said change measuring step comprises performing fluorophore assisted carbohydrate electrophoresis.

10. A method according to claim 9, said method further comprising the step of,
    visualizing said fluorophore assisted electrophoresis by a CCD.

11. A method according to claim 10, said method further comprising the step of,
    analyzing the image received by said CCD with a computer program.

12. A method according to claim 10, said method further comprising the step of,
    visualizing said fluorophore-assisted electrophoresis by photography.

13. A method according to claim 1, wherein said substrate comprises a label selected from the group consisting of 8-aminonapthalene-1,3,6-trisulphonic acid, 1-amino-6,8-disulphonic acid, 1-amino-4-naphthalene sulfonic acid, lucifer yellow, and 2-aminoacridone.

* * * * *